United States Patent
Hocek et al.

(10) Patent No.: US 10,414,788 B2
(45) Date of Patent: Sep. 17, 2019

(54) SUBSTITUTED THIENOPYRROLOPYRIMIDINE RIBONUCLEOSIDES FOR THERAPEUTIC USE

(71) Applicants: USTAV ORGANICKE CHEMIE A BIOCHEMIE AV CR, V.V.I., Prague (CZ); UNIVERZITA PALACKEHO V OLOMOUCI, Olomouc (CZ)

(72) Inventors: Michal Hocek, Prague (CZ); Michal Tichy, Vodochody (CZ); Marian Hajduch, Moravsky Beroun (CZ); Petr Dzubak, Brodek u Prerova (CZ)

(73) Assignees: USTAV ORGANICKE CHEMIE A BIOCHEMIE AV CR, V.V.I., Prague (CZ); UNIVERZITA PALACKEHO V OLOMOUCI, Olomouch (CZ)

( * ) Notice: Subject to any disclaimer, the term of this patent is extended or adjusted under 35 U.S.C. 154(b) by 0 days.

(21) Appl. No.: 16/098,068

(22) PCT Filed: Jun. 29, 2016

(86) PCT No.: PCT/CZ2016/050021
§ 371 (c)(1),
(2) Date: Oct. 31, 2018

(87) PCT Pub. No.: WO2018/001393
PCT Pub. Date: Jan. 4, 2018

(65) Prior Publication Data
US 2019/0144487 A1    May 16, 2019

(51) Int. Cl.
C07H 19/24    (2006.01)
A61P 35/00    (2006.01)

(52) U.S. Cl.
CPC ............. *C07H 19/24* (2013.01); *A61P 35/00* (2018.01)

(58) Field of Classification Search
None
See application file for complete search history.

(56) References Cited

FOREIGN PATENT DOCUMENTS

| | | |
|---|---|---|
| WO | 2009/089804 A1 | 7/2009 |
| WO | 2010/121576 A2 | 10/2010 |

OTHER PUBLICATIONS

Chung et al., Journal of Medicinal Chemistry, American Chemical Society, US, vol. 23 (11), Nov. 1980, pp. 1158-1166 (Year: 1980).*
International Search Report and Written Opinion for corresponding PCT application No. PCT/CZ2016/050021, dated Oct. 7, 2016.
Chung, Fung-Lung, et al., "Synthesis of Certain [6:5:6] Linear Tricyclic Nucleosides as Potential Antitumor Agents", Journal of Medicinal Chemistry, American Chemical Society, US, vol. 23, No. 11, Nov. 1, 1980, pp. 1158-1166.

* cited by examiner

*Primary Examiner* — Traviss C McIntosh, III
(74) *Attorney, Agent, or Firm* — Notaro, Michalos & Zaccaria P.C.

(57) ABSTRACT

A group of substituted thienopyrrolopyrimidine ribonucleosides of general formula I, in which R shows strong cytostatic and cytotoxic activities preferably against cancer cell lines of broad spectrum of diseases including tumors of various histogenetic origin.

10 Claims, No Drawings

SUBSTITUTED THIENOPYRROLOPYRIMIDINE RIBONUCLEOSIDES FOR THERAPEUTIC USE

FIELD OF THE INVENTION

The invention provides new type of compounds with anti-cancer activity and their therapeutic use.

BACKGROUND OF THE INVENTION

Despite the existence of tens of approved antiproliferation drugs, the treatment of many kinds of leukemia and other cancers is still not very successful. Thus the development of new type of compounds with anti-cancer properties is needed.

Recently our group discovered two new classes of cytostatic compounds, 7-(het)aryl-7-deazaadenosines (formula A, PCT/CZ2010/000050; Bourderioux, A. et al., *J. Med. Chem.* 2011, 54, 5498-5507) and 6-hetaryl-7-deazapurine ribonucleosides bearing hydrogen or fluorine in position 7 (formula B, PCT/CZ2009/000004; Nauš, P. et al., *J. Med. Chem.* 2010, 53, 460-470). Pyrimidoindole ribonucleosides and 8H-thieno[2',3':4,5]pyrrolo[2,3-d]pyrimidine ribonucleosides prepared in our group are the only known types of annulated deazapurine nucleosides, however, they displayed only minor or no cytotoxicity (formula C, ref.: Tichý, M. et al., *Bioorg. Med. Chem.* 2012, 20, 6123-6133; Tichý, M. et al., *Bioorg. Med. Chem.* 2013, 21, 5362-5372).

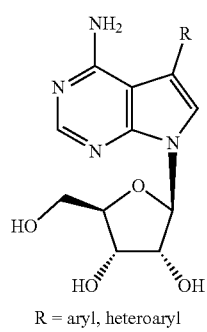

(A)

R = aryl, heteroaryl

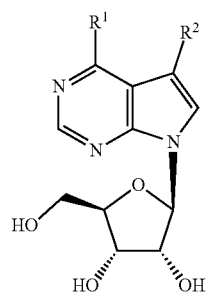

(B)

R¹ = aryl, heteroaryl
R² = H, halo, heteroaryl

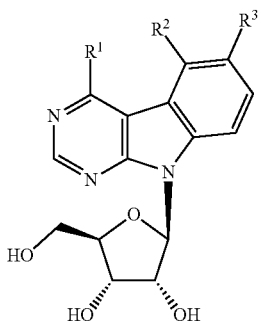

(C)

R¹ = NH₂, Me, MeNH₂, Me₂NH, cyclopropyl, heteroaryl, aryl
R² = H, Cl, heteroaryl
R³ = H, Cl, heteroaryl

SUMMARY OF THE INVENTION

This invention describes new 4-substituted 8H-thieno[3',2':4,5]pyrrolo[2,3-d]pyrimidine ribonucleosides exhibiting strong cytostatic and cytotoxic effects on cell lines preferentially of tumor origin and on broad spectrum of cancers of various histogenetic origin.

The specific fused-ring skeleton comprising heteroatoms in the specified locations makes these compounds significantly different from all previously prepared 7-deazapurine derivatives of general formulas A and B as well as from pyrimidoindole ribonucleosides of general formula C. Thienopyrrolopyrimidine bases themselves are a new class of compounds, which was not described previously. These compounds are unknown in nature. Hence, their biological activity has not yet been studied. Thienopyrrolopyrimidine nucleosides are a new and unique type of nucleosides with a rigid tricyclic base, which leads to a new type of interaction with biological systems and therefore to a different mechanism of action than all the other 7-substituted 7-deazapurine nucleosides exhibit.

This invention provides substituted thienopyrrolopyrimidine ribonucleosides of general formula I:

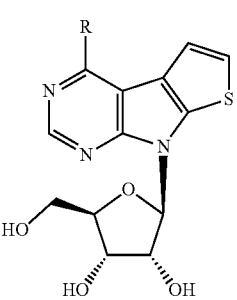

I wherein
R is selected from the group comprising
C1-C5 alkyl, optionally substituted by at least one substituent selected from hydroxy, sulfanyl, amino, C1-C5 alkoxy, C1-C5 sulfanyl, C1-C5 alkylamino, di(C1-C5 alkyl)amino;

C2-C6 alkenyl, optionally substituted by at least one substituent selected from hydroxy, sulfanyl, amino, C1-C5 alkoxy, C1-C5 sulfanyl, C1-C5 alkylamino, di(C1-C5 alkyl)amino;

C6-C12 aryl, optionally substituted by at least one substituent selected from C1-C5 alkyl, hydroxy, sulfanyl, amino, C1-C5 alkoxy, C1-C5 sulfanyl, C1-C5 alkylamino, di(C1-C5 alkyl)amino;

C4-12 heteroaryl, further comprising at least one heteroatom selected from O, S; optionally substituted by at least one substituent selected from C1-C5 alkyl, hydroxy, sulfanyl, amino, C1-C5 alkoxy, C1-C5 sulfanyl, C1-C5 alkylamino, di(C1-C5 alkyl)amino;

amino,
C1-C5 alkylamino,
di(C1-C5 alkyl)amino,
C1-C5 alkoxy,
C1-C5 alkylsulfanyl;
or a pharmaceutically acceptable salt thereof.

In one preferred embodiment, R is selected from the group comprising C1-C5 alkyl, phenyl, naphthyl, 2-furyl, 3-furyl, 2-thienyl, 3-thienyl, benzofuryl, dibenzofuryl, amino, C1-C5 alkylamino, di(C1-C5 alkyl) amino, C1-C5 alkoxy, C1-C5 alkylsulfanyl.

More preferably, R is selected from the group comprising furan-2-yl, furan-3-yl, benzofuran-2-yl, methylsulfanyl, methoxy, amino, dimethylamino or methyl.

Formula I includes all possible optical isomers of the compounds, and mixtures of optical isomers, including racemic mixtures.

As used herein and unless indicated otherwise, the substituent group names have the following meanings:

"alkyl" refers to a linear or branched-chain saturated hydrocarbyl chain, containing the number of carbons indicated at each relevant occurrence of this term;

"alkenyl" refers to a linear or branched-chain hydrocarbyl chain containing one or more double bonds, containing the number of carbons indicated at each relevant occurrence of this term;

"aryl" refers to a hydrocarbyl group comprising at least one aromatic ring and containing the number of carbons indicated at each relevant occurrence of this term. Aryl may also contain more than one ring, then the rings may be fused or non-fused;

"heteroaryl" refers to a substituent group comprising at least one aromatic ring and containing the number of carbons and the number and type of heteroatoms indicated at each relevant occurrence of this term. Heteroaryl may also contain more than one ring, then the rings may be fused or non-fused;

"hydroxy" refers to the group —OH;
"sulfanyl" refers to the group —SH;
"amino" refers to s the group —NH$_2$;
"alkylamino" refers to a group —NHR', wherein R' corresponds to the definition of "alkyl";
"dialkylamino" refers to a group —NHR'R", wherein R' and R" correspond to the definition of "alkyl". R' and R" can be the same or different;
"alkoxy" refers to a group —OR', wherein R' corresponds to the definition of "alkyl";
"alkylsulfanyl" refers to a group —SR', wherein R' corresponds to the definition of "alkyl".

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto (e.g., phenol or hydroxyamic acid). Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in Remington's Pharmaceutical Sciences, 20th ed., Mack Publishing Company, Easton, Pa., (1985), which is herein incorporated by reference.

In a preferred embodiment, the present invention provides the following thienopyrrolopyrimidine ribonucleosides of formula I:

4-(Furan-2-yl)-8-(β-D-ribofuranosyl)-8H-thieno[3',2':4,5]pyrrolo[2,3-d]pyrimidine 4-(Furan-3-yl)-8-(β-D-ribofuranosyl)-8H-thieno[3',2':4,5]pyrrolo[2,3-d]pyrimidine 4-(Benzofuran-2-yl)-8-(β-D-ribofuranosyl)-8H-thieno[3',2':4,5]pyrrolo[2,3-d]pyrimidine 4-Methyl-8-(β-D-ribofuranosyl)-8H-thieno[3',2':4,5]pyrrolo[2,3-d]pyrimidine 4-(N,N-dimethylamino)-8-(β-D-ribofuranosyl)-8H-thieno[3',2':4,5]pyrrolo[2,3-d]pyrimidine 4-Amino-8-(β-D-ribofuranosyl)-8H-thieno[3',2':4,5]pyrrolo[2,3-d]pyrimidine 4-Methoxy-8-(β-D-ribofuranosyl)-8H-thieno[3',2':4,5]pyrrolo[2,3-d]pyrimidine 4-(Methylsulfanyl)-8-(β-D-ribofuranosyl)-8H-thieno[3',2':4,5]pyrrolo[2,3-d]pyrimidine Additionally, the present invention provides a compound of formula I for use as a medicament.

The present invention provides substituted thienopyrrolopyrimidine ribonucleosides of formula I for use in inhibition of pathological cell proliferation of tumor/non-tumor origin and/or in a method of treatment of tumor/non-tumor disease associated with cell hyperproliferation.

The present invention provides substituted thienopyrrolopyrimidine ribonucleosides of formula I for the preparation of a medicament for treatment of tumor/cancer diseases, covering e.g. epithelial, mesenchymal and neuroectoderm origin tumors.

The present invention provides a method of treatment of tumor/cancer diseases, such as epithelial, mesenchymal and neuroectodermal origin tumors, comprising the step of administering at least one compound of formula I to a patient in need of such treatment.

The present invention provides a pharmaceutical composition comprising a therapeutically effective amount of at least one compound of formula I and one or more pharmaceutically acceptable carriers, fillers and/or excipients.

The invention also provides the above mentioned pharmaceutical composition for use in the inhibition of pathological cell proliferation of tumor/non-tumor origin and/or in the treatment of tumor/non-tumor disease associated with cell hyperproliferation.

The term "therapeutically effective amount" of a compound of the present invention refers to an amount of the compound of the present invention that will be effective in treating a disease or disorder in a human or mammalian. In the case of cancer treatment, therapeutically effective amount of drug can reduce the amount of cancer cells, the tumor size; inhibit (slow down to certain extent or preferably stop) cancer cell infiltration into peripheral organs; inhibit, i.e. slow down or stop tumor metastasis; inhibit at least to some extent tumor growth and/or relieve at least to some extent one or more symptoms associated with tumor or cancer.

As used herein, the term "pharmaceutical composition" refers to a formulation of a compound and a medium generally accepted in the art for the delivery of biologically active agents to a mammal, e.g. to a human Such a medium includes pharmaceutically acceptable carriers, diluents or adjuvants.

As used herein, the term "pharmaceutically acceptable carrier, filler or excipient" includes excipients, carriers, lubricants, sweetening agents, preservatives, dyes, flavoring agents, surfactants, disintegration agents, suspending agents, drug stabilizers, isotonic agents, solvents, or emulsifiers which have been approved for use in humans or domestic animals.

The invention further provides compounds of formula I for use in the form of an active substance of a pharmacologically acceptable composition, which can be made by common procedures known in the field, e.g. the active substance can be bound to or mixed with pharmaceutically acceptable inert organic and/or inorganic carriers/excipients.

The invention also provides compounds of formula I for use as a second or further active substance, which has synergistic effect with other active substances in known medicaments, or administration of compounds of formula I together with such medicaments.

In one embodiment, the present invention provides use of compounds of formula I as a prodrug or in other suitable form, which releases the active compound in vivo.

DETAILED DESCRIPTION OF THE INVENTION

Compounds Numbering
Following numbering of compounds is used:

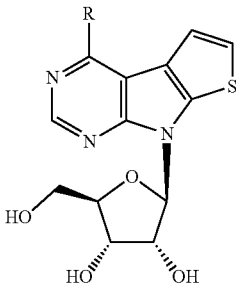

1a-h

R=

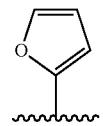

a

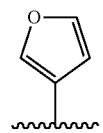

b

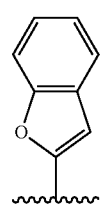

c d

e

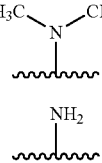

f

g

h

Synthesis of Compounds

Key-intermediate benzoylated 4-chlorothienopyrrolopyrimidine ribonucleoside 6 was synthesised by 4-step procedure starting from 4,6-dichloropyrimidine (2), which was zincated (Mosrin, M.; Knochel, P. *Chem. Eur. J.* 2009, 15, 1468-1477) and coupled with 3-iodothiphene to give 4,6- dichloro-5-thiophen-3-ylpyrimidine (3). Nucleophilic substitution with one equivalent of sodium azide in THF furnished azido derivative 4, which was photochemically cyclized to desired thienopyrrolopyrimidine 5. Vorbrüggen's glycosylation gave benzoylated 4-chlorothienopyrrolopyrimidine nucleoside 6 (Scheme 1).

Scheme 1: Synthesis of benzoylated thienopyrrolopyrimidine nucleoside 6

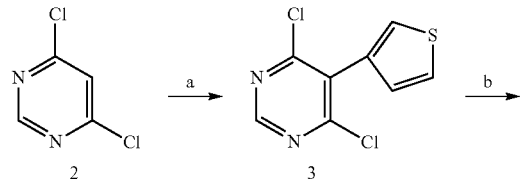

Reaction conditions: a: 1) (TMP)$_2$Zn·MgCl$_2$·2LiCl (0.55 eq.), THF, 0° C., 1 hr, then r.t., 1 hr; 2) 3-iodothiophene (1.2 eq.), Pd(PPh$_3$)$_4$ (0.1 eq.), THF, 65° C., 16 hr; b: NaN$_3$ (1 eq.), LiCl (1eq.), THF, r.t., 2 days; c: TFA, UV (254 nm), r.t., 2 days; d: BSA (1 eq.), MeCN, 60° C., 30 min; then 1-O-acetyl-2,3,4-tri-O-benzoyl-β-D-ribofuranose (2 eq.), TMSOTf (2 eq.), 60° C., 8 hr.

Target 4-substituted nucleosides (Scheme 2) were prepared by palladium-catalyzed reactions or nucleophilic substitutions. 2-Furyl group was introduced into position 4 by Stille coupling with 2-furyltributylstannane, 3-furyl and 2-benzofuryl groups by Suzuki reaction with corresponding boronic acids, methyl derivative was synthesised by palladium-catalyzed alkylation with trimethylalluminium and dimethylaminoderivative by nucleophilic substitution with dimethylamine. All these reactions led to benzoylated derivatives, which gave target free nucleosides by deprotection using sodium methoxide in methanol. Methoxy, amino and methylsulfanyl groups were introduced by nucleophilic substitution, benzoyl groups were deprotected under reaction conditions.

Scheme 2: Synthesis of 4-substituted thienopyrrolopyrimidine nucleosides 7, 1

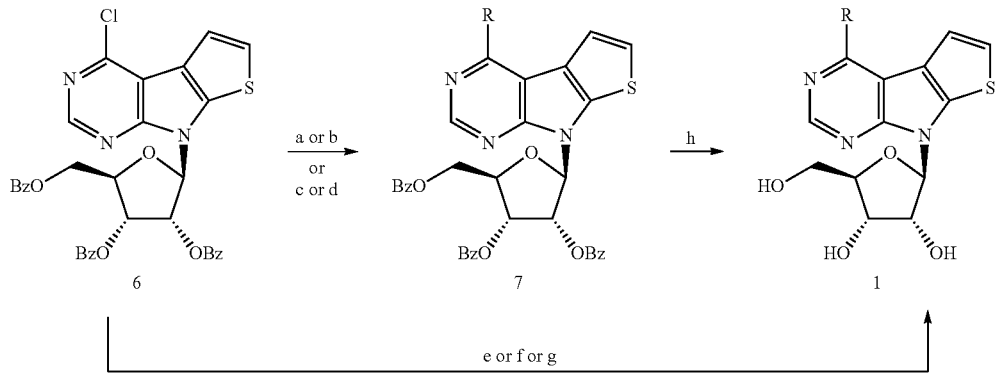

Reaction conditions: a: 2-tributylstannylfurane (1.2 eq.), PdCl$_2$(PPh$_3$)$_2$ (0.1 eq.), DMF, 100° C., 8 hr; b: R-boronic acid (1.5 eq.), Pd(PPh$_3$)$_4$ (0.05 eq.), K$_2$CO$_3$ (2 eq.), toluene, 100° C., 8 hr; c: Me$_3$Al (2 eq.), Pd(PPh$_3$)$_4$ (0.05 eq.), THF, r.t., 12 hr; d: Me$_2$NH in THF (2 eq.), propan-2-ol/EtOH 1:1, r.t., 24 hr; e: NH$_3$ (aq.), dioxane, 120° C., 12 hr; f: MeONa (1.3 eq.), MeOH, r.t., 12 hr; g: MeSNa (1.3 eq.), MeOH, r.t., 12 hr; h: 1M MeONa in MeOH (0.3 eq.), MeOH, r.t., 24 hr.

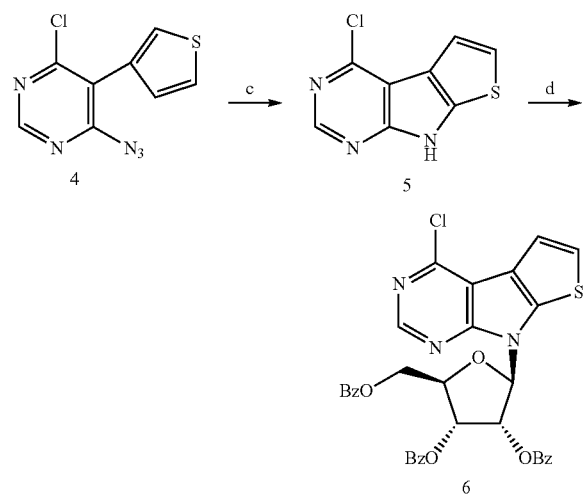

TABLE 1

Synthesis of 4-substituted thienopyrrolopyrimidine nucleosides 7, 1

| Entry | Conditions | R | Protected nucleoside | Yield [%] | Free nucleoside | Yield [%] |
|---|---|---|---|---|---|---|
| 1 | a | 2-furyl | 7a | 67 | 1a | 68 |
| 2 | b | 3-furyl | 7b | 82 | 1b | 83 |
| 3 | b | 2-benzofuryl | 7c | 83 | 1c | 86 |
| 4 | c | Me | 7d | — | 1d | 70 |
| 5 | d | Me$_2$N | 7e | 85 | 1e | 88 |
| 6 | e | NH$_2$ | — | — | 1f | 78 |
| 7 | f | MeO | — | — | 1g | 65 |
| 8 | g | MeS | — | — | 1h | 90 |

If tested compounds showed activity in in vitro cytotoxic test (Table 4), it was selective against broad spectrum of cancer cell lines of various histogenetic origin (mesenchymal or epitelial tumors) with significantly lower activity against normal human fibroblasts (BJ and MRC-5 cell lines). Active compounds showed promising therapeutic indexes (15-2500). $IC_{50}$ values of compounds 1c, 1f were in micromolar range, $IC_{50}$ values of compounds 1d, 1g, 1h, were sub-micromolar to nanomolar. Cytotoxic activity against cancer cells was independent on p53 gene status, same activities were found for HCT116 (p53 wild type) and for mutant line with deleted gene HCT116 (p53 −/−). However, number of derivatives showed lower cytotoxicity against cells overexpressing transport proteins (mdr-1 for K562-TAX line and mrp-1 for CEM-DNR).

EXAMPLES

List of Abbreviations
ATR Attenuated total reflectance
aq. aqueous
bd broad doublet
bq broad quartet
bs broad singlet
bt broad triplet
btd broad triplet of doublets
Bz benzoyl
C-18 C-18 reverse phase as stationary phase
calcd calculated
d doublet
dd doublet of doublets
ddd doublet of doublet of doublets
DMF N,N-dimethylformamide
DMSO dimethylsulfoxide
dt doublet of triplets
eq. equivalent
ESI electrospray ionization
EtOH ethanol
FT Fourier transform
HPFC high performance flash chromatography
HR high resolution
iPr isopropyl
IR infrared spectroscopy
m multiplet
Me methyl
MeCN acetonitrile
MeOH methanol
MeONa sodium methoxide
MeSNa sodium thiomethoxide
m.p. melting point
MS mass spectrometry
MTT 3-(4,5-dimethylthiazol-2-yl)-2,5-diphenyltetrazolium bromide
ν wave number
NMR nuclear magnetic resonance
Ph phenyl
q quartet
r.t. room temperature
s singlet
$SiO_2$ silicagel as stationary phase
t triplet
td triplet of doublets
TMSOTf trimethylsilyl trifluoromethansulfonate
TFA trifluoroacetic acid
THF tetrahydrofuran
$(TMP)_2Zn$ bis(2,2,6,6-tetramethypiperidinyl)zinc
General Experimental Part
NMR spectra were recorded on a 400 MHz ($^1H$ at 400 MHz, $^{13}C$ at 100.6 MHz), a 500 MHz ($^1H$ at 500 MHz, $^{13}C$ at 125.7 MHz), or a 600 MHz ($^1H$ at 600 MHz, $^{13}C$ at 150.9 MHz) spectrometer. Melting points were determined on a Kofler block and are uncorrected. Germicid UV bulb, model EUV-13B was used for photocyclization reactions. Optical rotations were measured at 25° C., and $[\alpha]_D^{20}$ values are given in $10^{-1}$ deg $cm^2$ $g^{-1}$. High resolution mass spectra were measured using electrospray ionization. Reverse-phase high performance flash chromatography (HPFC) was performed on KP-C18-HS columns with Biotage SP1 system. FT IR spectra were measured on Bruker Alpha spectrometer using ATR technique. The purity of all tested compounds was confirmed by HPLC analysis and was >95%.

TABLE 3

List of Compounds in Examples

| Example | Compound | Structure | Systematic name |
|---|---|---|---|
| 10 | 1a | 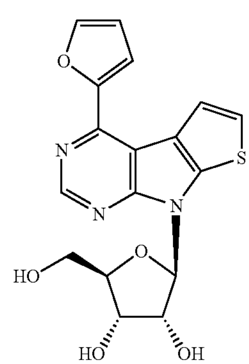 [SMILES: OC[C@H]1O[C@@H](n2c3ncnc(-c4ccco4)c3c3ccsc32)[C@H](O)[C@@H]1O] | 4-(Furan-2-yl)-8-(β-D-ribofuranosyl)-8H-thieno[3',2':4,5]pyrrolo[2,3-d]pyrimidine |

TABLE 3-continued

List of Compounds in Examples

| Example | Compound | Structure | Systematic name |
|---------|----------|-----------|-----------------|
| 11 | 1b | 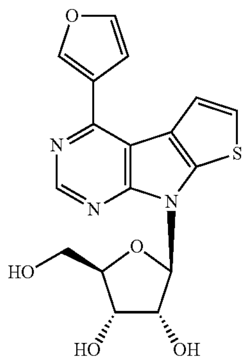 [SMILES: OC[C@H]1O[C@@H](n2c3ncnc(-c4ccoc4)c3c3ccsc32)[C@H](O)[C@@H]1O] | 4-(Furan-3-yl)-8-(β-D-ribofuranosyl)-8H-thieno[3',2':4,5]pyrrolo[2,3-d]pyrimidine |
| 12 | 1c | 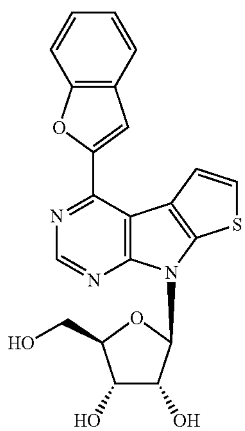 [SMILES: OC[C@H]1O[C@@H](n2c3ncnc(-c4cc5ccccc5o4)c3c3ccsc32)[C@H](O)[C@@H]1O] | 4-(Benzofuran-2-yl)-8-(β-D-ribofuranosyl)-8H-thieno[3',2':4,5]pyrrolo[2,3-d]pyrimidine |
| 13 | 1d | 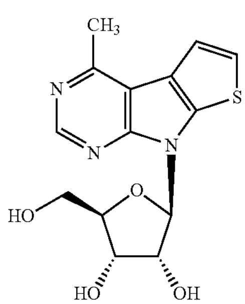 [SMILES: Cc1ncnc2c1c1ccsc1n2[C@@H]1O[C@H](CO)[C@@H](O)[C@H]1O] | 4-Methyl-8-(β-D-ribofuranosyl)-8H-thieno[3',2':4,5]pyrrolo[2,3-d]pyrimidine |
| 14 | 1e | 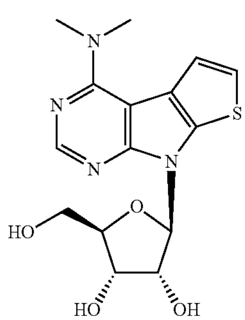 [SMILES: CN(C)c1ncnc2c1c1ccsc1n2[C@@H]1O[C@H](CO)[C@@H](O)[C@H]1O] | 4-(N,N-dimethylamino)-8-(β-D-ribofuranosyl)-8H-thieno[3',2':4,5]pyrrolo[2,3-d]pyrimidine |

TABLE 3-continued

List of Compounds in Examples

| Example | Compound | Structure | Systematic name |
|---|---|---|---|
| 15 | 1f | 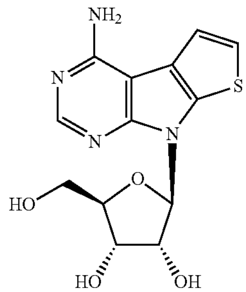 [SMILES: Nc1ncnc2c1c1ccsc1n2[C@@H]1O[C@H](CO)[C@@H](O)[C@H]1O] | 4-Amino-8-(β-D-ribofuranosyl)-8H-thieno[3',2':4,5]pyrrolo[2,3-d]pyrimidine |
| 16 | 1g | 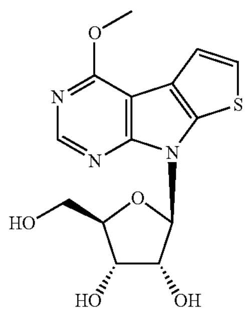 [SMILES: COc1ncnc2c1c1ccsc1n2[C@@H]1O[C@H](CO)[C@@H](O)[C@H]1O] | 4-Methoxy-8-(β-D-ribofuranosyl)-8H-thieno[3',2':4,5]pyrrolo[2,3-d]pyrimidine |
| 17 | 1h | 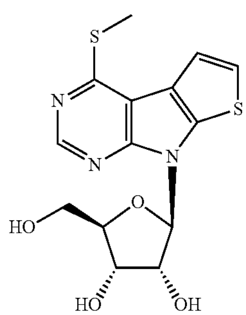 [SMILES: CSc1ncnc2c1c1ccsc1n2[C@@H]1O[C@H](CO)[C@@H](O)[C@H]1O] | 4-(Methylsulfanyl)-8-(β-D-ribofuranosyl)-8H-thieno[3',2':4,5]pyrrolo[2,3-d]pyrimidine |

General Procedure A (Zemplén Deprotection of Benzoylated Nucleosides):

Protected nucleoside was dissolved in methanol (10 ml) and 1M solution of MeONa in MeOH (0.3 equiv.) was added. Reaction mixture was stirred at r.t. overnight. Solvent was evaporated under reduced pressure and crude products were purified using RP-HPFC (H$_2$O/MeOH, 0%-100%, 2 L).

Example 1

4,6-Dichloro-5-(thiofen-3-yl)pyrimidine (3)

4,6-Dichloropyrimidine (2) was zincated according to modified literature procedure (Mosrin, M.; Knochel, Chem. Eur. J. 2009, 15, 1468-1477). 4,6-Dichloropyrimidine (2) (950 mg, 6.30 mmol) was dissolved in THF (10 ml) and added dropwise into an ice-cooled solution of (TMP)$_2$Zn.MgCl$_2$.LiCl in THF (0.35 M, 9.0 ml, 3.15 mmol) and the reaction mixture was stirred at 0° C. for 1 hour, then let to warm to r.t. for one hour and added to a solution of 3-iodothiophene (0.74 ml, 6.7 mmol) and Pd(PPh$_3$)$_4$ (775 mg, 0.67 mmol) in THF (3 ml), which was pre-stirred at r.t. for 20 min., and stirred at 65° for 16 hrs. Solvent was evaporated under reduced pressure and crude mixture was purified by HPFC (hexane/EtOAc 0→1%) to give 3 (890 mg, 58%) as a white solid. m.p. 178-180° C. IR (ATR): v=2932, 2862, 1510, 1404, 1326, 813, 774. $^1$H NMR (600.1 MHz, CDCl$_3$): 7.15 (dd, 1H, J$_{4,5}$=4.9, J$_{4,2}$=1.4, H-4-thienyl); 7.47 (dd, 1H, J$_{2,5}$=3.0, J$_{2,4}$=1.4, H-2-thienyl); 7.48 (dd, 1H, J$_{5,4}$=4.9, J$_{5,2}$=3.0, H-5-thienyl); 8.75 (s, 1H, H-2). $^{13}$C NMR (150.9 MHz, CDCl$_3$): 126.12 (CH-5-thienyl); 126.91 (CH-2-thienyl); 128.08 (CH-4-thienyl); 129.83 (C-5); 131.56 (C-3-thienyl); 156.44 (CH-2); 161.55 (C-4,6). APCI MS m/z (rel %): 231 (100) [M+H]. HR MS (APCI) for C$_8$H$_5$N$_2$Cl$_2$S [M+H]: calcd 230.95450; found 230.95456.

Example 2

4-Azido-6-chloro-5-(thiophen-3-yl)pyrimidine (4)

4,6-Dichloro-5-thiophen-3-ylpyrimidine (3) (1.1 g, 4.9 mmol) was dissolved in THF (10 ml), NaN$_3$ (320 mg, 4.9 mmol) and LiCl (204 mg, 4.9 mmol) were added and the reaction mixture was stirred for 2 days at r.t. Solvent was evaporated and the crude material was purified by column chromatography on silica (hexane/EtOAc 6:1). Desired product 4 (1.0 g, 90%) was obtained as a yellow solid. m.p.

85° C.; IR (ATR): v=3390, 3086, 2148 (weak), 1587, 1514, 1406, 1382, 1324, 1182, 1086, 978, 898, 816, 794, 763, 633, 504. $^1$H NMR (500.0 MHz, DMSO-$d_6$): 7.75 (dd, 1H, $J_{4,5}$=5.1, $J_{4,2}$=1.3, H-4-thienyl); 7.82 (dd, 1H, $J_{5,4}$=5.1, $J_{5,2}$=3.0, H-5-thienyl); 8.34 (dd, 1H, $J_{2,5}$=3.0, $J_{2,4}$=1.3, H-2-thienyl); 10.17 (s, 1H, H-2). $^{13}$C NMR (125.7 MHz, DMSO-$d_6$): 117.66 (C-5); 126.71 (CH-5-thienyl); 128.78 (CH-4-thienyl); 129.39 (C-3-thienyl); 130.22 (CH-2-thienyl); 137.98 (CH-2); 144.00, 150.95 (C-4,6).

Example 3

4-Chloro-8H-thieno[3',2':4,5]pyrrolo[2,3-d]pyrimidine (5)

Azide 4 (200 mg, 0.84 mmol)) was dissolved in TFA (20 ml) and stirred at r.t under irradiation by 4 W UV bulb for 24 h. UV bulb was placed inside the flask with the reaction mixture. Solvent was evaporated and the crude material was purified by HPFC (40 g silica cartridge, hexane/EtOAc, 20→30%) to give compound 5 (98 mg, 56%) as a white solid. m.p. 258-261° C. IR (ATR): v=3047, 2931, 2861, 2804, 2663, 1607, 1568, 1499, 1470, 1425, 1313, 1267, 1229, 1107, 1071, 917, 835, 783, 635. $^1$H NMR (500.0 MHz, DMSO-$d_6$): 7.41 (d, 1H, $J_{6,5}$=5.3, H-6); 7.50 (d, 1H, $J_{5,6}$=5.3, H-5); 8.65 (s, 1H, H-2); 13.23 (bs, 1H, NH). $^{13}$C NMR (125.7 MHz, DMSO-$d_6$): 111.11 (C-4a); 118.01 (CH-5); 119.59 (C-4b); 121.46 (CH-6); 142.54 (C-7a); 148.48 (C-4); 150.69 (CH-2); 156.69 (C-8a). APCI MS m/z (rel %): 209 (100) [M+H]. HR MS (APCI) for $C_8H_5N_3ClS$ [M+H]: calcd 209.98872; found 209.98874.

Example 4

4-Chloro-8-(2,3,5-tri-O-benzoyl-β-D-ribofuranosyl)-8H-thieno[3',2':4,5]pyrrolo[2,3-d]pyrimidine (6)

Tricyclic base 5 (150 mg; 0.7 mmol) was dissolved in MeCN (30 ml) and BSA (175 µl, 0.7 mmol) was added. The reaction mixture was heated at 60° C. for 30 minutes, then, TMSOTf (316 µl, 1.75 mmol) and 1-O-acetyl-2,3,5-tri-O-benzoyl-β-D-ribofuranose (724 mg, 1.4 mmol) were added. The mixture was heated to 60° C. for 12 hours. After cooling to r.t., the mixture was extracted with EtOAc and water, organic layer was washed with NaHCO$_3$ and again with water, dried over MgSO$_4$ and evaporated under reduced pressure. Crude product was purified using column chromatography (hexane/EtOAc, 15→35%). Protected nucleoside 6 (187 mg, 40%) was obtained as a white solid. m.p. 166-169° C. $^1$H NMR (500.0 MHz, DMSO-$d_6$): 4.72 (dd, 1H, $J_{gem}$=12.3 $J_{5'b,4'}$=4.6, H-5'b); 4.84 (dd, 1H, $J_{gem}$=12.3, $J_{5'a,4'}$=3.1, H-5'a); 5.03 (td, 1H, $J_{4',5'}$=4.6, 3.1, $J_{4',3'}$=4.6, H-4'); 6.11 (dd, 1H, $J_{3',2'}$=6.1, $J_{3',4'}$=4.6, H-3'); 6.32 (dd, 1H, $J_{2',3'}$=6.1, $J_{2',1'}$=5.7, H-2'); 6.96 (d, 1H, $J_{1',2'}$=5.7, H-1'); 7.43 (m, 2H, H-m-Bz); 7.47 (d, 1H, $J_{6,5}$=5.4, H-6); 7.48, 7.52 (2×m, 2×2H, H-m-Bz); 7.53 (d, 1H, $J_{5,6}$=5.4, H-5); 7.62, 7.66, 7.69 (3×m, 3×1H, H-p-Bz); 7.82, 7.95, 7.99 (3×m, 3×2H, H-o-Bz); 8.66 (s, 1H, H-2). $^{13}$C NMR (125.7 MHz, DMSO-$d_6$): 63.76 (CH$_2$-5'); 70.94 (CH-3'); 72.53 (CH-2'); 79.85 (CH-4'); 86.54 (CH-1'); 112.08 (C-4a); 117.97 (CH-5); 120.41 (C-4b); 123.39 (CH-6); 128.40, 128.76 (C-i-Bz); 128.85, 128.90, 128.99 (CH-m-Bz); 129.32 (C-i-Bz); 129.38, 129.46, 129.58 (CH-o-Bz); 133.73, 134.12 (CH-p-Bz); 140.99 (C-7a); 149.15 (C-4); 150.91 (CH-2); 155.64 (C-8a); 164.58, 164.90, 165.59 (CO-Bz). ESI MS m/z (rel %): 676 (100) [M+Na]. HR MS (ESI) for $C_{34}H_{24}N_3O_7ClSNa$ [M+Na]: calcd 676.09157; found 676.09181.

Example 5

4-(2-Furyl)-8-(2,3,5-tri-O-benzoyl-β-D-ribofuranosyl)-8H-thieno[3',2':4,5]pyrrolo[2,3-d]pyrimidine (7a)

Protected nucleoside 6 (200 mg, 0.31 mmol), 2-furyltributylstannane (131 mg, 0.38 mmol) and PdCl$_2$(PPh$_3$)$_2$ (22 mg, 0.03 mmol) were dissolved in anhydrous DMF (5 ml) and heated to 100° C. for 6-8 hours. The volatiles were removed in vacuo and the residue was loaded on silica column containing 15% of KF. Column was washed with 3 liters of hexane, than with gradient of ethyl-acetate in hexane (0→20%). Protected nucleoside 7a (140 mg, 67%) was obtained as a white solid. m.p. 114-118° C. IR (ATR): v=2933, 2862, 1722, 1605, 1562, 1446, 1435, 1289, 1264, 1134, 1110, 1091, 1055, 1029, 708, 687. $^1$H NMR (500.0 MHz, DMSO-$d_6$): 4.73 (dd, 1H, $J_{gem}$=12.4, $J_{5'b,4'}$=4.7, H-5'b); 4.84 (dd, 1H, $J_{gem}$=12.4, $J_{5'a,4'}$=3.1, H-5'a); 5.02 (td, 1H, $J_{4',5'}$=4.7, 3.1, $J_{4',3'}$=4.7, H-4'); 6.13 (dd, 1H, $J_{3',2'}$=6.1, $J_{3',4'}$=4.7, H-3'); 6.33 (dd, 1H, $J_{2',3'}$=6.1, $J_{2',1'}$=5.9, H-2'); 6.84 (dd, 1H, $J_{4,3}$=3.5, $J_{4,5}$=1.7, H-4-furyl); 7.00 (d, 1H, $J_{1',2'}$=5.9, H-1'); 7.40 (d, 1H, $J_{6,5}$=5.4, H-6); 7.42 (m, 2H, H-m-Bz); 7.47-7.56 (m, 5H, H-3-furyl, H-m-Bz); 7.62, 7.65, 7.70 (3×m, 3×1H, H-p-Bz); 7.81 (m, 2H, H-o-Bz); 7.93 (d, 1H, $J_{5,6}$=5.4, H-5); 7.99-8.02 (m, 4H, H-o-Bz); 8.24 (dd, 1H, $J_{5,4}$=1.7, $J_{5,3}$=0.8, H-5-furyl); 8.76 (s, 1H, H-2). $^{13}$C NMR (125.7 MHz, DMSO-$d_6$): 63.84 (CH$_2$-5'); 70.92 (CH-3'); 72.15 (CH-2'); 79.51 (CH-4'); 85.94 (CH-1'); 107.30 (C-4a); 112.99 (CH-4-furyl); 113.63 (CH-3-furyl); 121.21 (CH-6); 121.61 (CH-5); 121.71 (C-4b); 128.39, 128.80 (C-i-Bz); 128.91, 128.94, 129.04 (CH-m-Bz); 129.41 (C-i-Bz); 129.48, 129.62 (CH-o-Bz); 133.76, 134.16 (CH-p-Bz); 140.83 (C-7a); 145.22 (C-4); 146.86 (CH-5-furyl); 151.21 (CH-2); 152.36 (C-2-furyl); 156.98 (C-8a); 164.60, 164.96, 165.67 (CO-Bz). ESI MS m/z (rel %): 686 (45) [M+H]; 708 (100) [M+Na]. HR MS (ESI) for $C_{38}H_{28}N_3O_8S$ [M+H]: calcd 686.15916; found 686.15935.

Example 6

4-(3-Furyl)-8-(2,3,5-tri-O-benzoyl-β-D-ribofuranosyl)-8H-thieno[3',2':4,5]pyrrolo[2,3-d]pyrimidine (7b)

Protected nucleoside 6 (250 mg, 0.38 mmol), furan-3-boronic acid (85 mg, 0.76 mmol), K$_2$CO$_3$ (157 mg, 0.76 mmol) and Pd(PPh$_3$)$_4$ (22 mg, 0.019 mmol) were dissolved in toluene and heated to 100° C. for 6 hours. Solvent was evaporated and the crude product was purified by column chromatography (hexane/EtOAc, 0→20%). Nucleoside 7b containing 30% of impurities (312 mg, 83%) was obtained as a yellow solid and was directly deprotected. ESI MS m/z (rel %): 686 (19) [M+H]; 708 (100) [M+Na]. HR MS (ESI) for $C_{38}H_{27}N_3O_8SNa$ [M+Na]: calcd 708.14111; found 708.14120.

Example 7

4-(2-Benzofuryl)-8-(2,3,5-tri-O-benzoyl-β-D-ribofuranosyl)-8H-thieno[3',2':4,5]pyrrolo[2,3-d]pyrimidine (7c)

Compound 7c was prepared as described for 7b from protected nucleoside 6 (250 mg, 0.38 mmol) and benzofuran-2-boronic acid (124 mg, 0.76 mmol). Nucleoside 7c (228 mg, 82%) was obtained as a yellow solid. m.p. 110-113° C. IR (ATR): v=2965, 2938, 1728, 1603, 1454, 1433, 1290, 1267, 1112, 1070, 1030, 709, 688. $^1$H NMR (500.0 MHz, DMSO-d$_6$): 4.75 (dd, 1H, $J_{gem}$=12.4, $J_{5'b,4'}$=4.6, H-5'b); 4.86 (dd, 1H, $J_{gem}$=12.4, $J_{5'a,4'}$=3.1, H-5'a); 5.04 (td, 1H, $J_{4',5'}$=4.6, 3.1, $J_{4',3'}$=4.6, H-4'); 6.15 (dd, 1H, $J_{3',2'}$=6.1, $J_{3',4'}$=4.6, H-3'); 6.35 (dd, 1H, $J_{2',3'}$=6.1, $J_{2',1'}$=5.8, H-2'); 7.03 (d, 1H, $J_{1',2'}$=5.8, H-1'); 7.39 (ddd, 1H, $J_{5,4}$=8.0, $J_{5,6}$=7.3, $J_{5,7}$=1.0, H-5-benzofuryl); 7.42 (m, 2H, H-m-Bz); 7.45 (d, 1H, $J_{6,5}$=5.4, H-6); 7.48-7.55 (m, 5H, H-6-benzofuryl, H-m-Bz); 7.62, 7.64, 7.70 (3×m, 3×1H, H-p-Bz); 7.82 (m, 2H, H-o-Bz); 7.85 (ddd, 1H, $J_{4,5}$=8.0, $J_{4,6}$=1.3, $J_{4,7}$=1.0, H-4-benzofuryl); 7.93 (d, 1H, $J_{3,7}$=1.0, H-3-benzofuryl); 7.98 (dq, 1H, $J_{7,6}$=8.4, $J_{7,3}$=$J_{7,4}$=$J_{7,5}$=1.0, H-7-benzofuryl); 8.00, 8.01 (2×m, 2×2H, H-o-Bz); 8.08 (d, 1H, $J_{5,6}$=5.4, H-5); 8.86 (s, 1H, H-2). $^{13}$C NMR (125.7 MHz, DMSO-d$_6$): 63.88 (CH$_2$-5'); 70.97 (CH-3'); 72.26 (CH-2'); 79.61 (CH-4'); 86.08 (CH-1'); 108.58 (C-4a); 109.31 (CH-3-benzofuryl); 112.06 (CH-7-benzofuryl); 121.55 (C-4b); 121.68 (CH-6); 121.83 (CH-5); 122.76 (CH-4-benzofuryl); 124.21 (CH-5-benzofuryl); 126.82 (CH-6-benzofuryl); 127.83 (C-3a-benzofuryl); 128.42, 128.82 (C-i-Bz); 128.94, 128.97, 129.07 (CH-m-Bz); 129.42 (C-i-Bz); 129.50, 129.65 (CH-o-Bz); 133.79, 134.19 (CH-p-Bz); 141.60 (C-7a); 145.00 (C-4); 151.19 (CH-2); 153.99 (C-2-benzofuryl); 155.62 (C-7a-benzofuryl); 157.19 (C-8a); 164.65, 164.98, 165.70 (CO-Bz). ESI MS m/z (rel %): 758 (100) [M+Na]. HR MS (ESI) for C$_{42}$H$_{29}$N$_3$O$_8$S [M+H]: calcd 736.17481; found 736.17495.

Example 8

4-Methyl-8-(2,3,5-tri-O-benzoyl-β-D-ribofuranosyl)-8H-thieno[3',2':4,5]pyrrolo[2,3-d]pyrimidine (7d)

(Me)$_3$Al (345 μl, 2M in toluene) was added to a solution of nucleoside 6 (150 mg, 0.23 mmol) and Pd(PPh$_3$)$_4$ (12 mg, 0.012 mmol) in THF (8 ml) and the reaction mixture was stirred at 70° C. for 12 hr. Solvent was evaporated and purification by HPFC (hexane/EtOAc 10→50%) gave nucleoside 7d (137 mg, purity 90%), which was directly deprotected. ESI MS m/z (rel %): 634 (18) [M+H]; 656 (100) [M+Na]. HR MS (ESI) for C$_{35}$H$_{28}$N$_3$O$_7$S [M+H]: calcd 634.16425; found 634.16474.

Example 9

4-N,N-dimethylamino-8-(2,3,5-tri-O-benzoyl-β-D-ribofuranosyl)-8H-thieno[3',2':4,5]pyrrolo[2,3-d]pyrimidine (7e)

Dimethylamine (253 μl, 2M in THF) was added to a solution of nucleoside 11 (220 mg, 0.34 mmol) in isopropanol (15 ml) and the reaction mixture was stirred at r.t. for 24 hr. Solvent was evaporated and purification by HPFC (hexane/EtOAc 15%) gave nucleoside 7e (190 mg, 85%) as a white solid. m.p. 148-151° C. $^1$H NMR (500.0 MHz, DMSO-d$_6$): 3.35 (s, 6H, (CH$_3$)$_2$N); 4.70 (dd, 1H, $J_{gem}$=12.3, $J_{5'b,4}$=4.6, H-5'b); 4.81 (dd, 1H, $J_{gem}$=12.3, $J_{5'a,4'}$=3.1, H-5'a); 4.96 (td, 1H, $J_{4',5'}$=4.6, 3.1, $J_{4',3'}$=4.6, H-4'); 6.09 (dd, 1H, $J_{3',2'}$=6.1, $J_{3',4'}$=4.6, H-3'); 6.26 (t, 1H, $J_{2',1'}$=$J_{2',3'}$=6.1, H-2'); 6.90 (d, 1H, $J_{1',2'}$=6.1, H-1'); 7.23 (d, 1H, $J_{6,5}$=5.5, H-6); 7.39-7.44 (m, 3H, H-5, H-m-Bz); 7.51, 7.52 (2×m, 2×2H, H-m-Bz); 7.62, 7.678, 7.684 (3×m, 3×1H, H-p-Bz); 7.81, 7.97, 8.03 (3×m, 3×2H, H-o-Bz); 8.20 (s, 1H, H-2). $^{13}$C NMR (125.7 MHz, DMSO-d$_6$): 39.36 ((CH$_3$)$_2$N); 63.91 (CH$_2$-5'); 70.88 (CH-3'); 71.79 (CH-2'); 79.17 (CH-4'); 85.59 (CH-1'); 97.93 (C-4a); 119.86 (CH-6); 121.21 (CH-5); 122.04 (C-4b); 128.37, 128.79 (C-i-Bz); 128.96, 129.04 (CH-m-Bz); 129.46 (C-i-Bz); 129.49, 129.54, 129.60 (CH-o-Bz); 133.80, 134.15, 134.19 (CH-p-Bz); 135.17 (C-7a); 151.12 (CH-2); 156.29 (C-8a); 157.01 (C-4); 164.59, 164.97, 165.71 (CO-Bz). ESI MS m/z (rel %): 663 (15) [M+H]. 685 (100) [M+Na]. HR MS (ESI) for C$_{36}$H$_{31}$N$_4$O$_7$S [M+H]: calcd 663.19080; found 663.19088.

Example 10

4-(2-Furyl)-8-(β-D-ribofuranosyl)-8H-thieno[3',2':4,5]pyrrolo[2,3-d]pyrimidine (1a)

Compound 7a (140 mg, 0.20 mmol) was deprotected according to the general procedure A. Nucleoside 1a (52 mg, 68%) was obtained as a white solid. m.p. 189-192° C. [α]$_D$ −65.1 (c 0.19). IR (ATR): v=3242, 2930, 1579, 1548, 1504, 1420, 1401, 1331, 1127, 1099, 1041, 719. $^1$H NMR (500.0 MHz, DMSO-d$_6$): 3.63, 3.67 (2×bdd, 2×1H, $J_{gem}$=11.5, $J_{5',4'}$=5.2, H-5'); 3.98 (td, 1H, $J_{4',5'}$=5.2, $J_{4',3'}$=2.8, H-4'); 4.13 (dd, 1H, $J_{3',2'}$=5.4, $J_{3',4'}$=2.8, H-3'); 4.60 (dd, 1H, $J_{2',1'}$=7.1, $J_{2',3'}$=5.4, H-2'); 5.01 (bs, 1H, OH-5'); 5.35 (bs, 1H, OH-3'); 5.49 (bs, 1H, OH-2'); 6.48 (d, 1H, $J_{1',2'}$=7.1, H-1'); 6.85 (dd, 1H, $J_{4,3}$=3.5, $J_{4,5}$=1.7, H-4-furyl); 7.43 (d, 1H, $J_{6,5}$=5.4, H-6); 7.50 (dd, 1H, $J_{3,4}$=3.5, $J_{3,5}$=0.8, H-3-furyl); 7.96 (d, 1H, $J_{5,6}$=5.4, H-5); 8.25 (dd, 1H, $J_{5,4}$=1.7, $J_{5,3}$=0.8, H-5-furyl); 8.83 (s, 1H, H-2). $^{13}$C NMR (125.7 MHz, DMSO-d$_6$): 62.19 (CH$_2$-5'); 70.76 (CH-3'); 71.11 (CH-2'); 85.47 (CH-4'); 86.45 (CH-1'); 106.96 (C-4a); 112.97 (CH-4-furyl); 113.41 (CH-3-furyl); 121.09 (CH-5); 121.38 (CH-6); 121.41 (C-4b); 140.88 (C-7a); 145.00 (C-4); 146.68 (CH-5-furyl); 151.14 (C-2-furyl); 152.55 (CH-2); 157.45 (C-8a). ESI MS m/z (rel %): 396 (100) [M+Na]. HR MS (ESI) for C$_{17}$H$_{15}$N$_3$O$_5$SNa [M+Na]: calcd 396.06246; found 396.06251.

Example 11

4-(3-Furyl)-8-(β-D-ribofuranosyl)-8H-thieno[3',2':4,5]pyrrolo[2,3-d]pyrimidine (1b)

Crude compound 7b (300 mg, 70% purity, 0.31 mmol) was deprotected according to the general procedure A. Nucleoside 1b (95 mg, 83%) was obtained as white crystals. m.p. 192-195° C. [α]$_D$ −1.6 (c 0.19, DMSO). IR (ATR): v=3424, 3225, 3161, 1565, 1496, 1453, 1441, 1301, 1261, 1132, 1051, 1016, 878, 817, 795, 652, 643, 596. $^1$H NMR (500.0 MHz, DMSO-d$_6$): 3.62, 3.67 (2×ddd, 2×1H, $J_{gem}$=11.5, $J_{5',OH}$=5.5, $J_{5',4}$=5.2, H-5'); 3.98 (td, 1H, $J_{4',5'}$=5.2, $J_{4',3'}$=2.8, H-4'); 4.12 (ddd, 1H, $J_{3',2'}$=5.5, $J_{3',OH}$=4.6, $J_{3',4'}$=2.8, H-3'); 4.59 (ddd, 1H, $J_{2',1'}$=7.3, $J_{2',OH}$=6.3, $J_{2',3'}$=5.5, H-2'); 5.04 (t, 1H, $J_{OH,5'}$=5.5, OH-5'); 5.35 (d, 1H, $J_{OH,3'}$=4.6, OH-3'); 5.50 (d, 1H, $J_{OH,2'}$=6.3, OH-2'); 6.48 (d, 1H, $J_{1',2'}$=7.3, H-1'); 7.19 (dd, 1H, $J_{4,5}$=1.9, $J_{4,2}$=0.9, H-4-furyl); 7.43 (d, 1H, $J_{6,5}$=5.4, H-6); 7.62 (d, 1H, $J_{5,6}$=5.4, H-5); 7.96 (dd, 1H, $J_{5,4}$=1.9, $J_{5,2}$=1.6, H-5-furyl); 8.57 (dd, 1H, $J_{2,5}$=1.6, $J_{2,4}$=0.9, H-2-furyl); 8.86 (s, 1H, H-2). $^{13}$C NMR (125.7 MHz, DMSO-d$_6$): 62.24 (CH$_2$-5'); 70.82 (CH-3'); 71.22 (CH-2'); 85.54 (CH-4'); 86.54 (CH-1'); 109.79 (C-4a); 110.32 (CH-4-furyl); 119.50 (CH-5); 120.69 (C-4b); 121.74 (CH-6); 125.17 (C-3-furyl); 140.65 (C-7a); 144.42 (CH-2-furyl); 144.90 (CH-5-furyl); 149.34 (C-4); 151.29 (CH-2); 156.92 (C-8a). ESI MS m/z (rel %): 396 (100)

[M+Na]. HR MS (ESI) for $C_{17}H_{15}N_3O_5SNa$ [M+Na]: calcd 396.06246; found 396.06237.

Example 12

4-(2-Benzofuryl)-8-(β-D-ribofuranosyl)-8H-thieno[3',2':4,5]pyrrolo[2,3-d]pyrimidine (1c)

Compound 7c was deprotected according to the general procedure C. Nucleoside 1c (100 mg, 86%) was obtained as yellowish crystals. m.p. 118-119° C. $[\alpha]_D$ −29.6 (c 0.13). IR (ATR): ν=3259, 1563, 1494, 1435, 1300, 1276, 1129, 1054, 1044, 1025, 794, 744, 644, 599. $^1$H NMR (500.0 MHz, DMSO-d$_6$): 3.65, 3.69 (2×ddd, 2×1H, $J_{gem}$=11.5, $J_{5',OH}$=5.5, $J_{5',4'}$=5.2, H-5'); 3.99 (td, 1H, $J_{4',5'}$=5.2, $J_{4',3'}$=2.8, H-4'); 4.14 (ddd, 1H, $J_{3',2'}$=5.3, $J_{3',OH}$=4.7, $J_{3',4'}$=2.8, H-3'); 4.62 (ddd, 1H, $J_{2',1'}$=7.1, $J_{2',OH}$=6.3, $J_{2',3'}$=5.3, H-2'); 5.03 (t, 1H, $J_{OH,5'}$=5.5, OH-5'); 5.36 (d, 1H, $J_{OH,3'}$=4.7, OH-3'); 5.52 (d, 1H, $J_{OH,2'}$=6.3, OH-2'); 6.52 (d, 1H, $J_{1',2'}$=7.1, H-1'); 7.40 (ddd, 1H, $J_{5,4}$=7.9, $J_{5,6}$=7.2, $J_{5,7}$=1.0, H-5-benzofuryl); 7.50 (d, 1H, $J_{6,5}$=5.4, H-6); 7.52 (ddd, 1H, $J_{6,7}$=8.4, $J_{6,5}$=7.2, $J_{6,4}$=1.3, H-6-benzofuryl); 7.86 (ddd, 1H, $J_{4,5}$=7.9, $J_{4,6}$=1.3, $J_{4,7}$=1.0, H-4-benzofuryl); 7.95 (d, 1H, $J_{3,7}$=1.0, H-3-benzofuryl); 8.00 (dq, 1H, $J_{7,6}$=8.4, $J_{7,3}$=$J_{7,4}$=$J_{7,5}$=1.0, H-7-benzofuryl); 8.12 (d, 1H, $J_{5,6}$=5.4, H-5); 8.94 (s, 1H, H-2). $^{13}$C NMR (125.7 MHz, DMSO-d$_6$): 62.18 (CH$_2$-5'); 70.77 (CH-3'); 71.16 (CH-2'); 85.55 (CH-4'); 86.52 (CH-1'); 108.22 (C-4a); 109.12 (CH-3-benzofuryl); 112.07 (CH-7-benzofuryl); 121.27 (C-4b); 121.60 (CH-5,6); 122.72 (CH-4-benzofuryl); 124.20 (CH-5-benzofuryl); 126.73 (CH-6-benzofuryl); 127.88 (C-3a-benzofuryl); 141.64 (C-7a); 144.75 (C-4); 151.15 (CH-2); 154.19 (C-2-benzofuryl); 155.58 (C-7a-benzofuryl); 157.68 (C-8a). ESI MS m/z (rel %): 424 (31) [M+H]; 446 (100) [M+Na]. HR MS (ESI) for $C_{21}H_{17}N_3O_5S$ [M+H]: calcd 423.0889; found 423.0894.

Example 13

4-Methyl-8-(β-D-ribofuranosyl)-8H-thieno[3',2':4,5]pyrrolo[2,3-d]pyrimidine (1d)

Crude compound 7d (125 mg, 0.23 mmol) was deprotected according to the general procedure A. Nucleoside 1d (43 mg, 70%) was obtained as a white lyophilizate (water/tBuOH). m.p. 126-128° C. $[\alpha]_D$ −62.3 (c 0.20). IR (ATR): ν=3524, 3131, 2848, 1608, 1504, 1450, 1402, 1323, 1257, 1113, 1051, 654. $^1$H NMR (500.0 MHz, DMSO-d$_6$): 2.84 (s, 3H, CH$_3$); 3.58-3.67 (bm, 2H, H-5'); 3.95 (td, 1H, $J_{4',5'}$=5.1, $J_{4',3'}$=2.8, H-4'); 4.11 (dd, 1H, $J_{3',2'}$=5.3, $J_{3',4'}$=2.8, H-3'); 4.56 (dd, 1H, $J_{2',1'}$=7.2, $J_{2',3'}$=5.3, H-2'); 5.01 (bs, 1H, OH-5'); 5.34 (bs, 1H, OH-3'); 5.47 (bs, 1H, OH-2'); 6.41 (d, 1H, $J_{1',2'}$=7.2, H-1'); 7.42 (d, 1H, $J_{6,5}$=5.3, H-6); 7.63 (d, 1H, $J_{5,6}$=5.3, H-5); 8.73 (s, 1H, H-2). $^{13}$C NMR (125.7 MHz, DMSO-d$_6$): 22.28 (CH$_3$); 62.22 (CH$_2$-5'); 70.80 (CH-3'); 71.24 (CH-2'); 85.42 (CH-4'); 86.42 (CH-1'); 112.20 (C-4a); 118.75 (CH-5); 121.52 (C-4b); 121.83 (CH-6); 139.32 (C-7a); 151.25 (CH-2); 155.73 (C-8a); 157.35 (C-4). ESI MS m/z (rel %): 322 (25) [M+H]; 344 (100) [M+Na]. HR MS (ESI) for $C_{14}H_{15}N_3O_4S$ [M+H]: calcd 321.0783; found 321.0789.

Example 14

4-N,N-dimethylamino-8-(β-D-ribofuranosyl)-8H-thieno[3',2':4,5]pyrrolo[2,3-d]pyrimidine (1e)

Compound 7e (90 mg, 0.14 mmol) was deprotected according to the general procedure A. Nucleoside 1e (42 mg, 88%) was obtained as white crystals. m.p. 117° C. $[\alpha]_D$ −8.5 (c 0.16). IR (ATR): ν=3258, 1583, 1460, 1442, 1420, 1314, 1112, 1053, 787, 646. $^1$H NMR (500.0 MHz, DMSO-d$_6$): 3.34 (s, 6H, (CH$_3$)$_2$N); 3.59, 3.64 (2×dd, 2×1H, $J_{gem}$=11.6, $J_{5',4'}$=5.2, H-5'); 3.92 (td, 1H, $J_{4',5'}$=5.2, $J_{4',3'}$=3.0, H-4'); 4.08 (dd, 1H, $J_{3',2'}$=5.5, $J_{3',4'}$=3.0, H-3'); 4.55 (dd, 1H, $J_{2',1'}$=7.1, $J_{2',3'}$=5.5, H-2'); 5.07, 5.37 (2×bs, 3H, OH-2',3',5'); 6.35 (d, 1H, $J_{1',2'}$=7.1, H-1'); 7.27 (d, 1H, $J_{6,5}$=5.5, H-6); 7.44 (d, 1H, $J_{5,6}$=5.5, H-5); 8.23 (s, 1H, H-2). $^{13}$C NMR (125.7 MHz, DMSO-d$_6$): 39.39 ((CH$_3$)$_2$N); 62.29 (CH$_2$-5'); 70.82 (CH-3'); 71.00 (CH-2'); 85.20 (CH-4'); 86.80 (CH-1'); 97.76 (C-4a); 119.65 (CH-6); 120.88 (CH-5); 121.53 (C-4b); 135.58 (C-7a); 150.85 (CH-2); 156.55 (C-8a); 157.10 (C-4). ESI MS m/z (rel %): 351 (39) [M+H]; 373 (100) [M+Na]. HR MS (ESI) for $C_{15}H_{19}N_4O_4S$ [M+H]: calcd 351.11215; found 351.11223.

Example 15

4-Amino-8-(β-D-ribofuranosyl)-8H-thieno[3',2':4,5]pyrrolo[2,3-d]pyrimidine (1f)

Nucleoside 6 (280 mg, 0.42 mmol) was dissolved in dioxane (4 ml) and 30% aq. ammonia (12 ml) was added. The reaction mixture was heated in pressure glass vial at 100° C. for 24 hr, cooled and solvents were evaporated. Purification by RP-HPFC (water/methanol, 10→100%) gave compound 1f (107 mg, 78%) as white crystals. m.p. 98° C. $[\alpha]_D$ −24.7 (c 0.15). IR (ATR): ν=3452, 3347, 3073, 2933, 2862, 1723, 1605, 1551, 1453, 1263, 1093, 1068, 1028, 707. $^1$H NMR (500.0 MHz, DMSO-d$_6$): 3.58, 3.63 (2×bdd, 2×1H, $J_{gem}$=11.7, $J_{5',4'}$=5.0, H-5'); 3.92 (td, 1H, $J_{4',5'}$=5.0, $J_{4',3'}$=2.8, H-4'); 4.08 (ddd, 1H, $J_{3',2'}$=5.5, $J_{3',OH}$=4.3, $J_{3',4'}$=2.8, H-3'); 4.55 (ddd, 1H, $J_{2',1'}$=7.1, $J_{2',OH}$=6.5, $J_{2',3'}$=5.5, H-2'); 5.08 (bs, 1H, OH-5'); 5.25 (bd, 1H, $J_{OH,3'}$=4.3, OH-3'); 5.40 (bd, 1H, $J_{OH,2'}$=6.5, OH-2'); 6.26 (d, 1H, $J_{1',2'}$=7.1, H-1'); 7.18 (bs, 2H, NH$_2$); 7.26 (d, 1H, $J_{6,5}$=5.3, H-6); 7.82 (d, 1H, $J_{5,6}$=5.3, H-5); 8.16 (s, 1H, H-2). $^{13}$C NMR (125.7 MHz, DMSO-d$_6$): 62.33 (CH$_2$-5'); 70.89 (CH-3'); 71.22 (CH-2'); 85.22 (CH-4'); 86.77 (CH-1'); 96.80 (C-4a); 118.91 (CH-6); 119.96 (CH-5); 121.48 (C-4b); 135.57 (C-7a); 151.95 (CH-2); 155.89 (C-8a); 156.19 (C-4). ESI MS m/z (rel %): 323 (15) [M+H]; 345 (100) [M+Na]. HR MS (ESI) for $C_{13}H_{15}N_4O_7S$ [M+H]: calcd 323.08085; found 323.08091.

Example 16

4-Methoxy-8-(β-D-ribofuranosyl)-8H-thieno[3',2':4,5]pyrrolo[2,3-d]pyrimidine (1g)

Nucleoside 6 (130 mg, 0.20 mmol) was suspended in methanol (20 ml) and sodium methoxide (15 mg, 0.26 mmol) was added. The reaction mixture was stirred overnight at r.t., solvent was evaporated and crude material was purified by RP-HPFC chromatography (water/methanol 10→100%). Nucleoside 1g (43 mg, 65%) was obtained as white crystals. m.p. 159-160° C. $[\alpha]_D$ −47.3 (c 0.15, DMSO). IR (ATR): ν=3617, 3480, 2951, 1610, 1564, 1443, 1335, 1308, 1205, 1127, 1052, 1023, 975, 635, 602. $^1$H NMR (500.0 MHz, DMSO-d$_6$): 3.60, 3.64 (2×ddd, 2×1H, $J_{gem}$=11.6, $J_{5',OH}$=5.6, $J_{5',4'}$=5.1, H-5'); 3.95 (td, 1H, $J_{4',5'}$=5.1, $J_{4',3'}$=2.8, H-4'); 4.10 (dd, 1H, $J_{3',2'}$=5.3, $J_{3',OH}$=4.7, $J_{3',4'}$=2.8, H-3'); 4.13 (s, 3H, CH$_3$O); 4.55 (dd, 1H, $J_{2',1'}$=7.1, $J_{2',OH}$=6.4, $J_{2',3'}$=5.3, H-2'); 5.01 (t, 1H, $J_{OH,5'}$=5.6, OH-5'); 5.32 (d, 1H, $J_{OH,3'}$=4.7, OH-3'); 5.47 (d, 1H, $J_{OH,2'}$=6.4, OH-2'); 6.38 (d, 1H, $J_{1',2'}$=7.1, H-1'); 7.38 (d, 1H, $J_{5,6}$=5.3, H-5); 7.39 (d, 1H, $J_{6,5}$=5.3, H-6); 8.53 (s, 1H, H-2). $^{13}$C NMR (125.7 MHz, DMSO-d$_6$): 54.11 (CH$_3$O); 62.22 (CH$_2$-5'); 70.80 (CH-3'); 71.29 (CH-2'); 85.42 (CH-4'); 86.72 (CH-1'); 99.35 (C-4a); 118.11 (CH-5); 120.51 (C-4b); 122.00 (CH-6); 137.53 (C-7a); 151.17 (CH-2); 157.17 (C-8a); 161.53 (C-4). ESI MS m/z (rel %): 360 (100) [M+Na]. HR MS (ESI) for C$_{14}$H$_{15}$N$_3$O$_5$SNa [M+Na]: calcd 360.06246; found 360.06254.

Example 17

4-Methylsulfanyl-8-(β-D-ribofuranosyl)-8H-thieno[3',2':4,5]pyrrolo[2,3-d]pyrimidine (1h)

Nucleoside 6 (80 mg, 0.12 mmol) was suspended in methanol (10 ml) and sodium thiomethoxide (12 mg, 0.16 mmol) was added. The reaction mixture was stirred overnight at r.t., solvent was evaporated and crude material was purified by RP-HPFC chromatography (water/methanol 10→100%). Nucleoside 1h (33 mg, 90%) was obtained as white crystals. m.p. 148-152° C. [α]$_D$ −50.9 (c 0.16). IR (ATR): ν=3305, 1576, 1556, 1497, 1471, 1431, 1321, 1265, 1246, 1136, 1094, 1055, 912, 821, 719, 645. $^1$H NMR (500.0 MHz, DMSO-d$_6$): 2.74 (s, 3H, CH$_3$S); 3.61, 3.64 (2×dd, 2×1H, $J_{gem}$=11.6, $J_{5',4'}$=5.2, H-5'); 3.96 (td, 1H, $J_{4',5'}$=5.2, $J_{4',3'}$=2.8, H-4'); 4.11 (dd, 1H, $J_{3',2'}$=5.3, $J_{3',4'}$=2.8, H-3'); 4.55 (dd, 1H, $J_{2',1'}$=7.1, $J_{2',3'}$=5.3, H-2'); 4.90-5.70 (bm, 3H, OH-2',3',5'); 6.38 (d, 1H, $J_{1',2'}$=7.1, H-1'); 7.43 (d, 1H, $J_{5,6}$=5.3, H-5); 7.45 (d, 1H, $J_{6,5}$=5.3, H-6); 8.73 (s, 1H, H-2). $^{13}$C NMR (125.7 MHz, DMSO-d$_6$): 11.57 (CH$_3$S); 62.19 (CH$_2$-5'); 70.77 (CH-3'); 71.33 (CH-2'); 85.49 (CH-4'); 86.54 (CH-1'); 110.05 (C-4a); 118.07 (CH-5); 120.83 (C-4b); 122.46 (CH-6); 138.67 (C-7a); 151.00 (CH-2); 153.70 (C-8a); 159.00 (C-4); ESI MS m/z (rel %): 376 (100) [M+Na]. HR MS (ESI) for C$_{14}$H$_{16}$N$_3$O$_4$S$_2$ [M+H]: calcd 354.05767; found 354.05772.

In Vitro Antitumor Activity

MTT test was used for in vitro evaluation of antitumor activities of newly synthesized compounds on cell lines derived from normal tissues or tumors. Specifically, cell lines K562 (human acute myeloid leukemia), K562-Tax (human acute myeloid leukemia, paclitaxel resistant subline, overexpress multiple drug resistant protein PgP), CEM (T-lymfoblastic leukemia), CEM-DNR-bulk (T-lymfoblastic leukemia, doxorubicin resistant), A549 (human lung adenocarcinoma), HCT116 wt (human colorectal cancer, wild-type), HCT116p53−/−(human colorectal cancer, mutant p53) a U2OS (human bone osteosarcoma) were used.

Express characteristics, susceptibility profiles of classic antitumor drugs as well as methodology of cytotoxic MTT test have been repeatedly published {ref.:Noskova, V.; Dzubak, P.; Kuzmina, G.; Ludkova, A.; Stehlik, D.; Trojanec, R.; Janostakova, A.; Korinkova, G.; Mihal, V.; Hajduch, M., *Neoplasma* 2002, 49, 418-425}.

Results of Biological Testing:

The tested compounds showed activity in in vitro cytotoxic test (Table 4), and it was selective against broad spectrum of cancer cell lines of various histogenetic origin (mesenchymal or epitelial tumors) with significantly lower activity against normal human fibroblasts (BJ and MRC-5 cell lines were tested). Active compounds showed promising therapeutic indexes (15-2500). IC$_{50}$ values of compounds 1c, if were in micromolar range, IC$_{50}$ values of compounds 1d, 1g, 1h were sub-micromolar to nanomolar. Cytotoxic activity against cancer cells was independent on p53 gene status, same activities were found for HCT116 (p53 wild type) and for mutant line with deleted gene HCT116 (p53 −/−). However, a number of derivatives showed lower cytotoxicity against cells overexpressing transport proteins (mdr-1 for K562-TAX line and mrp-1 for CEM-DNR).

TABLE 4

Cytotoxic activities of prepared compounds

| Compound | A549 | CCRF-CEM | CEM-DNR | HCT116 | HCT116p53 | K562 | K562-TAX | U2OS |
|---|---|---|---|---|---|---|---|---|
| 1a | E | E | E | E | E | E | E | E |
| 1b | E | E | E | E | E | E | E | E |
| 1c | E | D | D | E | E | E | D | E |
| 1d | B | A | E | B | B | A | C | A |
| 1e | E | E | E | E | E | E | E | E |
| 1f | E | B | E | E | C | E | B | B |
| 1g | C | A | E | B | B | B | D | A |
| 1h | B | A | E | A | B | B | D | A |

IC$_{50}$: A = 10-200 nmol · l$^{-1}$;
B = 200-900 nmol · l$^{-1}$;
C = 0.9-10 μmol · l$^{-1}$;
D = 10-25 μmol · l$^{-1}$;
E = 25-50 μmol · l$^{-1}$.

INDUSTRIAL APPLICABILITY

In particular, the compounds of this invention can be used as medicaments or components of medicaments for treatment of cancer and leukemia.

The invention claimed is:
1. Substituted thienopyrrolopyrimidine ribonucleosides of general formula I

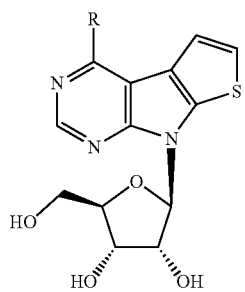

I wherein
R is selected from the group consisting of:
C1-C5 alkyl, optionally substituted by at least one substitutent selected from hydroxy, sulfanyl, amino, C1-C5 alkoxy, C1-C5 sulfanyl, C1-C5 alkylamino, and di(C1-C5 alkyl)amino;

C2-C6 alkenyl, optionally substituted by at least one substitutent selected from hydroxy, sulfanyl, amino, C1-C5 alkoxy, C1-C5 sulfanyl, C1-C5 alkylamino, and di(C1-C5 alkyl)amino;

C6-C12 aryl, optionally substituted by at least one substitutent selected from C1-C5 alkyl, hydroxy, sulfanyl, amino, C1-C5 alkoxy, C1-C5 sulfanyl, C1-C5 alkylamino, and di(C1-C5 alkyl)amino;

C4-12 heteroaryl, further comprising at least one heteroatom selected from O and S; optionally substituted by at least one substitutent selected from C1-C5 alkyl, hydroxy, sulfanyl, amino, C1-C5 alkoxy, C1-C5 sulfanyl, C1-C5 alkylamino, and di(C1-C5 alkyl)amino;

amino,
C1-C5 alkylamino,
di(C1-C5 alkyl)amino,
C1-C5 alkoxy, and
C1-C5 alkylsulfanyl;

or a pharmaceutically acceptable salt thereof, or an optical isomer thereof; or a mixture of optical isomers.

2. Substituted thienopyrrolopyrimidine ribonucleosides of general formula I according to claim 1, wherein R is selected from the group consisting of: C1-C5 alkyl, phenyl, naphthyl, 2-furyl, 3-furyl, 2-thienyl, 3-thienyl, benzofuryl, dibenzofuryl, amino, C1-C5 alkylamino, di(C1-C5 alkyl)amino, C1-C5 alkoxy, and C1-C5 alkylsulfanyl.

3. Substituted thienopyrrolopyrimidine ribonucleosides of general formula I according to claim 1, wherein R is selected from the group consisting of: furan-2-yl, furan-3-yl, benzofuran-2-yl, methylsulfanyl, methoxy, amino, dimethylamino and methyl.

4. Thienopyrrolopyrimidine ribonucleosides of general formula I of claim 1 being selected from the following compounds:

4-(Furan-2-yl)-8-((3-D-ribofuranosyl)-8H-thieno[3',2':4,5]pyrrolo[2,3-d]pyrimidine, 4-(Furan-3-yl)-8-((3-D-ribofuranosyl)-8H-thieno[3',2':4,5]pyrrolo[2,3-d]pyrimidine, 4-(Benzofuran-2-yl)-8-((3-D-ribofuranosyl)-8H-thieno[3',2':4,5]pyrrolo[2,3-d]pyrimidine, 4-Methyl-8-((3-D-ribofuranosyl)-8H-thieno[3',2':4,5]pyrrolo[2,3-d]pyrimidine, 4-(N,N-dimethylamino)-8-((3-D-ribofuranosyl)-8H-thieno[3',2':4,5]pyrrolo[2,3-d]pyrimidine, 4-Amino-8-((3-D-ribofuranosyl)-8H-thieno[3',2':4,5]pyrrolo[2,3-d]pyrimidine, 4-Methoxy-8-((3-D-ribofuranosyl)-8H-thieno[3',2':4,5]pyrrolo[2,3-d]pyrimidine, and 4-(Methylsulfanyl)-8-((3-D-ribofuranosyl)-8H-thieno[3',2':4,5]pyrrolo[2,3-d]pyrimidine.

5. A method of inhibition of pathological cell proliferation of tumor/non-tumor origin, comprising the step of administering the compound of general formula I according to claim 1 to a subject in need thereof.

6. A method of treatment of a tumor disease, comprising the step of administering the compound of general formula I according to claim 1 to a subject in need thereof.

7. A pharmaceutical composition characterized in that it comprises at least one compound of general formula I according to claim 1 and at least one pharmaceutically acceptable carrier, filler and/or excipient.

8. A pharmaceutical composition according to claim 7 for use in the inhibition of pathological cell proliferation of tumor/non-tumor origin and/or in the treatment of tumor/non tumor disease associated with cell hyperproliferation.

9. A method of treatment of tumor/non-tumor disease associated with cell hyperproliferation, comprising the step of administering the compound of general formula I according to claim 1 to a subject in need thereof.

10. The method according to claim 6, wherein the tumor disease is selected from the group consisting of tumors of epitelial, mesenchymal and neuroectodermal origin.

* * * * *